United States Patent [19]
Ollar et al.

[11] Patent Number: 5,962,306
[45] Date of Patent: Oct. 5, 1999

[54] METHOD OF DETERMINING THE PRESENCE OR ABSENCE OF A NONPARAFFINOPHILIC MICROORGANISM IN A SPECIMEN AND AN ASSOCIATED APPARATUS

[75] Inventors: Robert-A. Ollar, Milford; Mitchell S. Felder, Hermitage, both of Pa.

[73] Assignee: Infectech, Inc., Sharon, Pa.

[21] Appl. No.: 09/003,833

[22] Filed: Jan. 7, 1998

Related U.S. Application Data

[60] Division of application No. 08/858,350, May 19, 1997, Pat. No. 5,854,013, which is a continuation-in-part of application No. 08/528,189, Sep. 14, 1995, Pat. No. 5,721,112.

[51] Int. Cl.$^6$ .................................................. C12M 1/24
[52] U.S. Cl. .................................. 435/287.9; 435/288.1; 435/288.3
[58] Field of Search .................................. 435/29, 32, 34, 435/33, 39, 40, 287.1, 287.9, 288.1, 288.3, 304.1, 305.1, 307.1, 309.1

[56] References Cited

U.S. PATENT DOCUMENTS

| | | |
|---|---|---|
| 3,826,717 | 7/1974 | Gilbert et al. . |
| 3,966,552 | 6/1976 | Pagano et al. ........................ 435/288.1 |
| 4,048,016 | 9/1977 | Otto . |
| 4,252,897 | 2/1981 | Axford et al. ........................ 435/287.3 |
| 4,683,195 | 7/1987 | Mullis et al. . |
| 4,683,201 | 7/1987 | Hamill et al. . |
| 4,683,202 | 7/1987 | Mullis . |
| 4,859,586 | 8/1989 | Eisenberg et al. .................... 435/288.1 |
| 5,153,119 | 10/1992 | Ollar ......................................... 435/34 |
| 5,316,918 | 5/1994 | Ollar . |
| 5,374,538 | 12/1994 | Bratthall .................................... 435/36 |
| 5,677,169 | 10/1997 | Ollar et al. ............................ 435/288.1 |
| 5,750,363 | 5/1998 | Ollar et al. ............................ 435/288.1 |

FOREIGN PATENT DOCUMENTS

| | | | |
|---|---|---|---|
| 2525233 | 10/1983 | France ................................ 435/288.1 |

OTHER PUBLICATIONS

Fuhs, G.W., "Der Mikrobielle Abbau Von Kohlenwasserstoffen", *Arch. Mikrobiol.*, 39:374–422 (1961).

Mishra, S.K. et al., "Observations On Paraffin Baiting As A Laboratory Diagnostic Procedure In Nocardiosis", *Mycopathologica and Mycologia Applicatia*, vol. 51, 2–3, pp. 147–157 (1973).

Ollar, R.–A., "A Paraffin Baiting Technique That Enables A Direct Microscopic View Of "in situ" Morphology Of *Nocardia asteroides* With The Acid–Fast Or Fluorescence Staining Process", *Zbl, Bakt, Hyg., I. Abt. Orig. A 234*, pp. 81–90 (1976).

Wolinsky, E., "Nontuberculous Mycobacteria And Associated Diseases", *American Review of Respiratory Disease*, vol. 119: 107–159 (1979).

Horsburgh, C.R., Jr. et al., "Disseminated Infection with *Mycobacterium avium–intracellulare*", *Medicine*, vol. 64, No. 1: 36–48 (1983).

Murphey, S.A. et al., "*Mycobacterium Avium–Intracellulare* In A Hospital Hot Water System: Epidemiologic Investigation", *American Society for Microbiology*, 277 (1983).

(List continued on next page.)

*Primary Examiner*—William H. Beisner
*Attorney, Agent, or Firm*—David V. Radack; Eckert Seamans Cherin & Mellott, LLC

[57] ABSTRACT

A method of determining the presence or absence of a nonparaffinophilic microorganism in a specimen taken from a patient includes providing a receptacle containing an aqueous solution that does not contain a carbon source and inoculating the aqueous solution with the specimen. A slide having bound thereto a carbon source is placed into the receptacle. By analyzing the slide after exposure to the specimen, the presence or absence of a nonparaffinophilic microorganism in the specimen can be determined. An associated apparatus is also disclosed.

35 Claims, 1 Drawing Sheet

OTHER PUBLICATIONS

Kirihara, J.M. et al., "Improved Detection Times For *Mycobacterium avium* Complex And *Mycobacterium tuberculosis* With The BACTEC Radiometric System", *Journal of Clinical Microbiology*, pp. 841–845 (Nov. 1985).

Reichert, C.M. et al., "Pathologic Features Of Aids", *Aids: Etiology, Diagnosis, Treatment and Prevention*, pp. 111 and 134, J.B. Lippincott Company (1985).

Hawkins, C.C. et al., "*Mycobacterium avium* Complex Infections In Patients With The Acquired Immunodeficiency Syndrome", *Annals of Internal Medicine*, 105: 184–188 (1986).

Gonzalez, R. et al., "Evaluation Of Gen–Probe DNA Hybridization Systems For The Identification Of *Mycobacterium tuberculosis* And *Mycobacterium avium–intracellulare*", *Diagn. Microbiol. Infect. Dis.*, 8: 69–77 (1987).

Klatt, E.C. et al., "Pathology Of *Mycobacterium avium–intracellulare* Infection In Acquired Immunodeficiency Syndrome", *Human Pathology*, vol. 18, No. 7: 709–714 (Jul. 1987).

Wallace, J.M. et al., "*Mycobacterium avium* Complex Infection In Patients With The Acquired Immunodeficiency Syndrome* A Clinicopathologic Study", *Chest*, 93 (5), pp. 926–932 (1988).

Heifets, L. et al., "Comparison Of Bactericidal Activities Of Streptomycin, Amikacin, Kanamycin, And Capreomycin Against *Mycobacterium avium* And *Mycobacterium tuberculosis*", *Antimicrobial Agents and Chemotherapy*, pp. 1298–1301 (Aug. 1989).

Hurley, S.S. et al., "Development Of A Diagnostic Test For Johne's Disease Using A DNA Hybridization Probe", *Journal of Clinical Microbiology*, pp. 1582–1587 (Jul. 1989).

Horsburgh, C.R., Jr. et al., "The Epidemiology Of Disseminated Nontuberculous Mycobacterial Infection In The Acquired Immunodeficiency Syndrome (AIDS)", *American Review of Respiratory Disease*, 139: 4–7 (1989).

Ma, P. et al., "Definitive Diagnostic Methods For Diseases Indicative Of AIDS", *AIDS and Infections of Homosexual Men*, Second Edition, pp. 233–234 Butterworth Publishers (1989).

Hoy, J. et al, "Quadruple–Drug Therapy For *Mycobacterium avium–intracellulare* Bacteremia In AIDS Patients", *The Journal of Infectious Diseases*, 161: 801–805 (Apr. 1990).

Inderlied, C.B. et al., "Disseminated *Mycobacterium avium* Complex Infection", *AIDS Clinical Review*, pp. 165–191 (1990).

Kemper, C.A. et al., "Microbiologic And Clinical Response Of Patients With AIDS and MAC Bacteremia To A Four Oral Drug Regimen", *American Society for Microbiology*, (Abstract), p. 297 (1990).

Ollar, R.–A. et al., "The Use Of Paraffin Wax Metabolism In The Speciation Of *Mycobacterium avium–intracellulare*", *Tubercle*, 71, pp. 23–28, Longman Group UK, Ltd. (1990).

Bermudez, L.E. et al., "An Animal Of *Mycobacterium avium* Complex Disseminated Infection After Colonization Of The Intestinal Tract", *The Journal of Infectious Diseases*, 165: 75–79 (Jan. 1992).

Havlik, J.A., Jr. et al., "Disseminated *Mycobacterium avium* Complex Infection: Clinical Identification And Epidemiologic Trends", *The Journal of Infectious Diseases*, 165: 577–580 (Mar. 1992).

Kemper, C.A. et al., "Treatment Of *Mycobacterium avium* Complex Bacteremia In AIDS With A Four–Drug Oral Regimen", *Annals of Internal Medicine*, 116, No. 6: 466–472 (Mar. 1992).

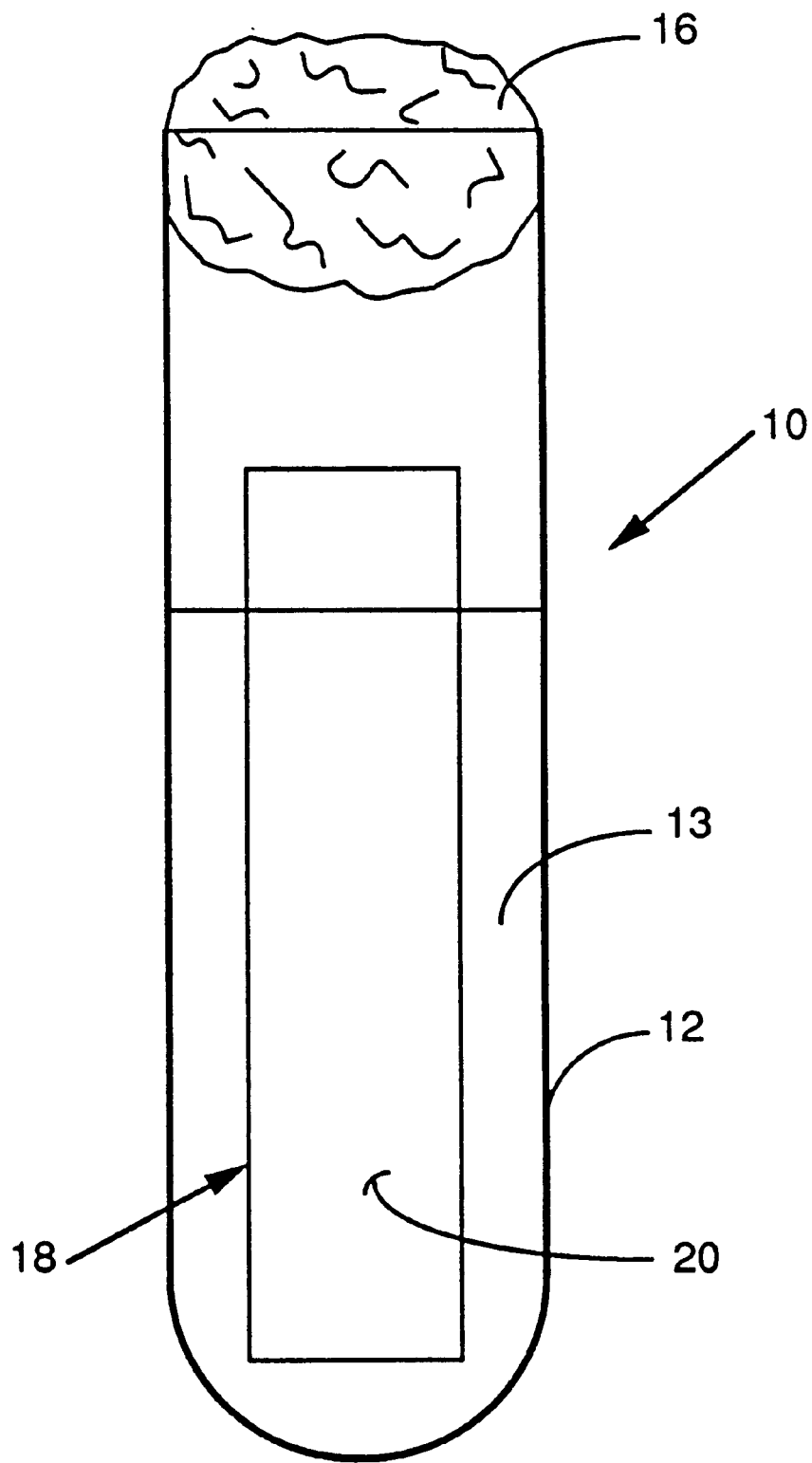

METHOD OF DETERMINING THE PRESENCE OR ABSENCE OF A NONPARAFFINOPHILIC MICROORGANISM IN A SPECIMEN AND AN ASSOCIATED APPARATUS

CROSS-REFERENCE TO RELATED APPLICATION

This is a divisional of U.S. patent application Ser. No. 08/858,350 filed May 19, 1997, now U.S. Pat. No. 5,854,013, which in turn is a continuation-in-part of U.S. Ser. No. 08/528,189 filed Sep. 14, 1995, now U.S. Pat. No. 5,721,112.

BACKGROUND OF THE INVENTION

This invention relates to a method of determining the presence or absence of a nonparaffinophilic microorganism in a specimen and an associated apparatus.

Identification of nonparaffinophilic microorganisms in a clinical specimen is an important part of medical treatment of patients. Often times, educated guesses as to the nature of the microorganism involved are made. It thus would be beneficial to improve the process of identifying these microorganisms with a simple, effective method and apparatus.

As used herein, the term "nonparaffinophilic microorganism" means any microorganism sustained by a carbon source other than paraffin. Examples of such nonparaffinophilic microorganisms include, but are not limited to, the following: *Mycobacterium tuberculosis; Mycobacterium paratuberculosis; Mycobacterium leprae*; Staphylococcus; Streptococcus; *E. coli*; Listeria; Brucellae; Humemophilus; Treponema; Pneumococcus; Clostridium; Cryptococcus; Coccidioides; Histoplasma; *Klebsiella pneumoniae*; Shigella spp.; Salmonella spp.; Salmonella; *E. coli* (0157); and *Helicobacter pylori*. Also, as used herein, the term "patient" refers to a member of the animal kingdom, including human beings, whose body specimen is being processed by the method and apparatus of the invention.

U.S. Pat. Nos. 5,153,119 and 5,316,918 disclose methods and apparatus for identifying and testing the antibiotic sensitivity of *Mycobacterium avium-intracellulare* ("MAI"), a paraffinophilic microorganism. The inventor named on those patents is Robert-A. Ollar, one of the co-inventors of the invention disclosed herein. This method involves providing a receptacle containing an aqueous solution and inoculating into the solution a specimen. After this, a paraffin coated slide is placed into the receptacle. The slide is then observed for the presence or absence of growth of MAI.

Despite the efficient, effective and economical method disclosed in Dr. Ollar's patents, there still remains a need for a simple and effective method to determine the presence or absence of a nonparaffinophilic microorganism.

SUMMARY OF THE INVENTION

The invention has met or exceeded the above-mentioned needs as well as others. A method of determining the presence or absence of a nonparaffinophilic microorganism in a specimen taken from a patient comprises providing a receptacle containing an aqueous solution that does not contain a carbon source and inoculating the aqueous solution with the specimen. A slide having bound thereto a carbon source is placed into the receptacle. By analyzing the slide after exposure to the specimen, the presence or absence of a nonparaffinophilic microorganism in the specimen can be determined.

An associated apparatus is also disclosed. The apparatus comprises a receptacle for holding an aqueous solution that does not contain a carbon source and a slide having bound thereto a carbon source adapted to be placed in the receptacle. The carbon source can be included in a gelatinous matrix which is bound to the slide or can be an ionically or affinity bound carbon source bound to a plurality of gel beads that are themselves adhered to the slide.

BRIEF DESCRIPTION OF THE DRAWING

A full understanding of the invention can be gained from the following detailed description of the invention when read in conjunction with the accompanying lone drawing which shows a front elevational view of a test tube holding a slide coated with a carbon source in an aqueous solution inoculated with a specimen.

DETAILED DESCRIPTION

The method and apparatus of the invention provide an efficient, effective and economical way of identifying a nonparaffinophilic microorganism. Referring now to the lone FIGURE, an embodiment of a nonparaffinophilic microorganism identification apparatus 10 is shown. The apparatus 10 includes a standard test tube 12 which contains an aqueous solution 13 (such as Czapek broth) and a cotton plug 16 to seal the test tube 12. According to the invention, a specimen to be tested for the presence or absence of a nonparaffinophilic microorganism is inoculated into the aqueous solution 13. A slide 18 having bound thereto a carbon source 20 is then placed into the test tube 12. It will be appreciated that the aqueous solution 13 should not contain any carbon source, as it is desired to provide a sole carbon source 20 on the slide 18 in order to effectively grow the nonparaffinophilic microorganism to be identified on the slide 18 and not in the aqueous solution 13. Growth on the slide 18, which can either be seen or unseen by the unaided human eye, can be analyzed to determine the presence or absence of a nonparaffinophilic microorganism. Preferably, a minimum of twenty-four (24) hours incubation time is necessary for growth to occur. In order to analyze the slide 18 after the incubation period, the slide 18 can be scraped using a flame sterilized spatula and subcultured on an agar-like tryptic soy agar ("TSA"). If the scrapings include growth, the growth on the TSA can be analyzed using classical microbiological procedures or can be analyzed using a DNA extraction process involving either organic solvent extraction or column chromatographic extraction.

The specimen to be inoculated into the test tube 12 can be a blood sample; any biopsy or tissue specimen; stomach fluid; urine; cerebral spinal fluid; nasopharyngeal mucosa or saliva. These specimens can be obtained from the patient in the doctor's office or in the emergency room of a hospital, for example, by known techniques in known standard ways.

The carbon source 20 on the slide 18 can include a gelatinous matrix containing a carbon source. A carbon source can be one or more of those selected from the group consisting of glucose, fructose, glycerol, mannitol, asparagine, casein, adonitol, l-arabinose, cellobiose, dextrose, dulcitol, d-galactose, inositol, inulin, lactose, levulose (d-fructose), maltose, d-mannitol, d-mannose, melibiose, raffinose, rhamnose, sucrose, salicin, d-sorbitol, trehalose and d-xylose, among others. Another embodiment can include providing a slide and coating the slide with an adhesive and securing a plurality of gel beads to the adhesive. The carbon source can then be either ionically or affinity bound to the gel beads.

The slide 18 with the gelatinous matrix containing a carbon source can be prepared by the following method. A receptacle, such as a laboratory beaker, is first filled with 100 ml of distilled water. Into the beaker is placed two (2) grams of agar (the gelatinous matrix) and three (3) grams of a carbon source (such as glucose). This mixture is then boiled and steam sterilized and the molten gelatinous matrix with a carbon source is poured into a petri dish, which is sitting on a hot plate. In this way the gelatinous matrix/carbon source remains molten. After this, a sterile slide 18 is dropped into the molten gelatinous matrix/carbon source and becomes coated therewith. The now coated slide is removed from the petri dish and allowed to stand for a minute or two in order to solidify the coating 20 thereon. The slide with the coating of a gelatinous matrix containing a carbon source is then ready to be placed in the test tube 12 containing the aqueous solution 13 and the specimen.

An alternative method of preparing the slide involves first coating the slide with an adhesive, such as collodion and then applying a plurality of gel beads (commercially available from Pharmacia of Parsippany, N.J.) to the adhesive. The gel beads are approximately one micron in diameter. The slide containing the coating of gel beads is now immersed in a buffering agent containing the carbon source (such as glucose) to attach the carbon source to the gel beads either ionically or affinity-wise.

Nonparaffinophilic microorganisms that can be identified using the method of the invention include any microorganism sustained by a carbon source other than paraffin. Nonparaffinophilic microorganisms include, but are not limited to, *Mycobacterium tuberculosis; Mycobacterium paratuberculosis; Mycobacterium leprae*; Staphylococcus; Streptococcus; *E. coli*; Listeria; Brucellae; Humemophilus; Treponema; Pneumococcus; Clostridium; Cryptococcus; Coccidioides; Histoplasma; *Klebsiella pneumoniae*; Shigella spp.; Salmonella spp.; Salmonella; *E. coli* (0157); and *Helicobacter pylori.*

In order to further elucidate the invention, the following examples are provided.

EXAMPLE 1

A patient visits a doctor with symptoms which the doctor believes indicates the presence of *staphylococcus aureus*. In order to determine the presence or absence of the *staphlococcus aureus*, a receptacle containing an aqueous solution comprising:

Distilled Water 1 liter
Beef Extract 1 gram
Peptone 10 grams
NaCl 75 grams
Phenol Red 0.025 grams is prepared. A specimen from each patient is inoculated into the receptacle. After this, a slide with bound d-mannitol thereon is placed into the receptacle. After a period of time, if a growth is not observed on the slide, the doctor determines that *staphylococcus aureus* is not present. If a growth is detected within a predetermined period of time, the doctor can be fairly sure that staphylococcal growth is present. Further confirmation of this identification can be made by conventional or molecular based systems.

EXAMPLE 2

A patient visits a doctor with symptoms which the doctor believes indicates the presence of *streptococcus pneumoniae*. In order to determine the presence or absence of the *streptococcus pneumoniae*, a receptacle containing an aqueous solution comprising:

Distilled Water 1 liter
Beef Infusion 450 grams
Proteose 20 grams
NaCl 5 grams is prepared. A specimen from each patient is inoculated into the receptacle. After this, a slide with bound dextrose thereon is placed into the receptacle. After a period of time, if a growth is not observed on the slide, the doctor determines that *streptococcus pneumoniae* is not present. If a growth is detected within a predetermined period of time, the doctor can be fairly sure that *streptococcus pneumoniae* growth is present. Further confirmation of this identification can be made by conventional or molecular based systems.

EXAMPLE 3

A patient visits a doctor with symptoms which the doctor believes indicates the presence of shigella spp. In order to determine the presence or absence of the shigella spp., a receptacle containing an aqueous solution comprising:

Distilled Water 1 liter
Beef Extract 5 grams
Peptone 5 grams
Bile Salts 8.5 grams
Sodium Citrate 8.5 grams
Sodium Thiosulfate 8.5 grams
Ferric Citrate 1 gram
Brilliant Green 0.33 milligrams
Neutral Red 0.025 grams is prepared. A specimen from each patient is inoculated into the receptacle. After this, a slide with bound lactose thereon is placed into the receptacle. After a period of time, if a growth is not observed on the slide, the doctor determines that shigella spp. is not present. If a growth is detected within a predetermined period of time, the doctor can be fairly sure that shigella spp. growth is present. Further confirmation of this identification can be made by conventional or molecular based systems.

EXAMPLE 4

A patient visits a doctor with symptoms which the doctor believes indicates the presence of salmonella spp. In order to determine the presence or absence of the salmonella spp., a receptacle containing an aqueous solution comprising:

Distilled Water 1 liter
Beef Extract 5 grams
Peptone 5 grams
Bile Salts 8.5 grams
Sodium Citrate 8.5 grams
Sodium Thiosulfate 8.5 grams
Ferric Citrate 1 gram
Brilliant Green 0.33 milligrams
Neutral Red 0.025 grams is prepared. A specimen from each patient is inoculated into the receptacle. After this, a slide with bound lactose thereon is placed into the receptacle. After a period of time, if a growth is not observed on the slide, the doctor determines that salmonella spp. is not present. If a growth is detected within a predetermined period of time, the doctor can be fairly sure that salmonella spp. growth is present. Further confirmation of this identification can be made by conventional or molecular based systems.

EXAMPLE 5

A patient visits a doctor with symptoms which the doctor believes indicates the presence of salmonella. In order to determine the presence or absence of the salmonella, a receptacle containing an aqueous solution comprising:

Distilled Water 1 liter
Tryptone 5 grams
Sodium Selenite 4 grams
Sodium Phosphate 10 grams is prepared. A specimen from each patient is inoculated into the receptacle. After this, a slide with bound lactose thereon is placed into the receptacle. After a period of time, if a growth is not observed on the slide, the doctor determines that salmonella is not present. If a growth is detected within a predetermined period of time, the doctor can be fairly sure that salmonella growth is present. Further confirmation of this identification can be made by conventional or molecular based systems.

EXAMPLE 6

A patient visits a doctor with symptoms which the doctor believes indicates the presence of E. coli. In order to determine the presence or absence of the E. coli, a receptacle containing an aqueous solution comprising:

Distilled Water 1 liter
Oxgall 5 grams
Peptone 20 grams
Brom Cresol Purple 0.01 grams is prepared. A specimen from each patient is inoculated into the receptacle. After this, a slide with bound lactose thereon is placed into the receptacle. After a period of time, if a growth is not observed on the slide, the doctor determines that E. coli is not present. If a growth is detected within a predetermined period of time, the doctor can be fairly sure that E. coli growth is present. Further confirmation of this identification can be made by conventional or molecular based systems.

EXAMPLE 7

A patient visits a doctor with symptoms which the doctor believes indicates the presence of E. coli (0157). In order to determine the presence or absence of the E. coli (0157), a receptacle containing an aqueous solution comprising:

Distilled Water 1 liter
Oxgall 5 grams
Peptone 20 grams
Brom Cresol Purple 0.01 grams is prepared. A specimen from each patient is inoculated into the receptacle. After this, a slide with bound sorbitol thereon is placed into the receptacle. After a period of time, if a growth is not observed on the slide, the doctor determines that E. coli (0157) is not present. If a growth is detected within a predetermined period of time, the doctor can be fairly sure that E. coli (0157) growth is present. Further confirmation of this identification can be made by conventional or molecular based systems.

EXAMPLE 8

A patient visits a doctor with symptoms which the doctor believes indicates the presence of helicobacter pylori. In order to determine the presence or absence of the helicobacter pylori, a receptacle containing an aqueous solution comprising:

Distilled Water 1 liter
Peptone 1 gram
NaCl 5 grams
Potassium Phosphate, Monobasic 2 grams
Urea 20 grams
Phenol Red 0.012 grams is prepared. A specimen from each patient is inoculated into the receptacle. After this, a slide with bound dextrose thereon is placed into the receptacle. After a period of time, if a growth is not observed on the slide, the doctor determines that helicobacter pylori is not present. If a growth is detected within a predetermined period of time, the doctor can be fairly sure that helicobacter pylori growth is present. Further confirmation of this identification can be made by conventional or molecular based systems.

EXAMPLE 9

A patient visits a doctor with symptoms which the doctor believes indicates the presence of klebsiella pneumoniae. In order to determine the presence or absence of the klebsiella pneumoniae, a receptacle containing an aqueous solution comprising:

Distilled Water 1 liter
Peptone 10 grams
Dipotasium Phosphate 2 grams
Eosin Y 0.4 grams
Methylene Blue 0.065 grams is prepared. A specimen from each patient is inoculated into the receptacle. After this, a slide with bound sucrose thereon is placed into the receptacle. After a period of time, if a growth is not observed on the slide, the doctor determines that klebsiella pneumoniae is not present. If a growth is detected within a predetermined period of time, the doctor can be fairly sure that klebsiella pneumoniae growth is present. Further confirmation of this identification can be made by conventional or molecular based systems.

It will be appreciated that a method of determining the presence or absence of a nonparaffinophilic microorganism in a specimen and an associated apparatus has been disclosed. The method is effective and efficient and does not involve the use of expensive and complicated equipment. An associated apparatus is also disclosed.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. An apparatus to facilitate determination of the presence or absence of a nonparaffinophilic microorganism in a specimen taken from a patient, said apparatus comprising:

a receptacles;
an aqueous solution contained in said receptacle, said aqueous solution having no carbon source therein; and
a slide having bound thereto a carbon source other than paraffin, at least a portion of said carbon source being immersed in said aqueous solution.

2. The apparatus of claim 1, wherein
said nonparaffinophilic microorganism is *staphylococcus aureus*; and
said carbon source is d-mannitol.
3. The apparatus of claim 2, wherein
said aqueous solution includes distilled water, beef extract, peptone, sodium chloride and phenol red.
4. The apparatus of claim 3, wherein
said aqueous solution includes 1 liter distilled water, 1 gram beef extract, 10 grams peptone, 75 grams sodium chloride and 0.025 grams phenol red.
5. The apparatus of claim 1, wherein
said nonparaffinophilic microorganism is *streptococcus pneumoniae*; and
said carbon source is dextrose.
6. The apparatus of claim 5, wherein
said aqueous solution includes distilled water, beef infusion, proteose and sodium chloride.
7. The apparatus of claim 6, wherein
said aqueous solution includes 1 liter distilled water, 450 grams beef infusion, 20 grams proteose and 5 grams sodium chloride.
8. The apparatus of claim 1, wherein
said nonparaffinophilic microorganism is shigella spp.; and
said carbon source is lactose.
9. The apparatus of claim 8, wherein
said aqueous solution includes distilled water, beef extract, peptone, bile salts, sodium citrate, sodium thiosulfate, ferric citrate, brilliant green and neutral red.
10. The apparatus of claim 9, wherein
said aqueous solution includes 1 liter distilled water, 5 grams beef extract, 5 grams peptone, 8.5 grams bile salts, 8.5 grams sodium citrate, 8.5 grams sodium thiosulfate, 1 gram ferric citrate, 0.33 milligrams brilliant green and 0.025 gram neutral red.
11. The apparatus of claim 1, wherein
said nonparaffinophilic microorganism is salmonella spp.; and
said carbon source is lactose.
12. The apparatus of claim 11, wherein
said aqueous solution includes distilled water, beef extract peptone, bile salts, sodium citrate, sodium thiosulfate, ferric citrate, brilliant green and neutral red.
13. The apparatus of claim 12, wherein
said aqueous solution includes 1 liter distilled water, 5 grams beef extract, 5 grams peptone, 8.5 grams bile salts, 8.5 grams sodium citrate, 8.5 grams sodium thiosulfate, 1 gram ferric citrate, 0.33 milligrams brilliant green and 0.025 grams neutral red.
14. The apparatus of claim 1, wherein
said nonparaffinophilic microorganism is salmonella; and
said carbon source is lactose.
15. The apparatus of claim 14, wherein
said aqueous solution includes distilled water, tryptone, sodium selenite and sodium phosphate.
16. The apparatus of claim 15, wherein
said aqueous solution includes 1 liter distilled water, 5 grams tryptone, 4 grams sodium selenite and 10 grams sodium phosphate.
17. The apparatus of claim 1, wherein
said nonparaffinophilic microorganism is *E. coli*; and
said carbon source is lactose.
18. The apparatus of claim 17, wherein
said aqueous solution includes distilled water, oxgall, peptone and brom cresol purple.
19. The apparatus of claim 18, wherein
said aqueous solution includes 1 liter distilled water, 5 grams oxgall, 20 grams peptone and 0.01 grams brom cresol purple.
20. The apparatus of claim 1, wherein
said nonparaffinophilic microorganism is *E. coli* (0157); and
said carbon source is sorbitol.
21. The apparatus of claim 20, wherein
said aqueous solution includes distilled water, oxgall, peptone and brom cresol purple.
22. The apparatus of claim 21, wherein
said aqueous solution includes 1 liter distilled water, 5 grams oxgall, 20 grams peptone and 0.01 grams brom cresol purple.
23. The apparatus of claim 1, wherein
said nonparaffinophilic microorganism is *helicobacter pylori*; and
said carbon source is dextrose.
24. The apparatus of claim 23, wherein
said aqueous solution includes distilled water, peptone, sodium chloride, potassium phosphate (monobasic), urea and phenol red.
25. The apparatus of claim 24, wherein
said aqueous solution includes 1 liter distilled water, 1 gram peptone, 5 grams sodium chloride, 2 grams potassium phosphate (monobasic), 20 grams urea and 0.012 grams phenol red.
26. The apparatus of claim 1, wherein
said nonparaffinophilic microorganism is *klebsiella pneumoniae*; and
said carbon source is sucrose.
27. The apparatus of claim 26, wherein
said aqueous solution includes distilled water, peptone, dipotasium phosphate, eosin Y and methylene blue.
28. The apparatus of claim 27, wherein
said aqueous solution includes 1 liter distilled water, 10 grams peptone, 2 grams dipotasium phosphate, 0.4 grams eosin Y and 0.065 grams methylene blue.
29. The apparatus of claim 1, wherein
said slide is coated with a gelatinous matrix containing said carbon source.
30. The apparatus of claim 1, wherein
said slide is coated with a plurality of gel beads which have bound thereon said carbon source.
31. The apparatus of claim 30, wherein
said carbon source is ionically bound to said gel beads.
32. The apparatus of claim 30, wherein
said carbon source is affinity bound to said gel beads.
33. The apparatus of claim 30, wherein
said gel beads are adhered to said slide by an adhesive.
34. The apparatus of claim 33, wherein
said adhesive is collodion.
35. The apparatus of claim 1, wherein
said carbon source is one or more of the group consisting of glucose, fructose, glycerol, mannitol, asparagine, casein, adonitol, l-arabinose, cellobiose, dextrose, dulcitol, d-galactose, inositol, inulin, lactose, levulose (d-fructose), maltose, d-mannitol, d-mannose, melibiose, raffinose, rhamnose, sucrose, salicin, d-sorbitol, trehalose and d-xylose.

* * * * *

UNITED STATES PATENT AND TRADEMARK OFFICE
CERTIFICATE OF CORRECTION

PATENT NO. : 5,962,306

DATED : October 5, 1999

INVENTOR(S) :
Robert-A. Ollar, et al.

It is certified that error appears in the above-identified patent and that said Letters Patent is hereby corrected as shown below:

Col. 6, line 62, "receptacles" should read --receptacle--.

Col. 7, line 43, place a comma (,) between "extract" and "peptone".

Signed and Sealed this

Twenty-second Day of May, 2001

Attest:

NICHOLAS P. GODICI

Attesting Officer     Acting Director of the United States Patent and Trademark Office